US00PP23340P2

(12) United States Plant Patent
Pan

(10) Patent No.: US PP23,340 P2
(45) Date of Patent: Jan. 22, 2013

(54) ***LANTANA* PLANT NAMED 'LANZ0001'**

(50) Latin Name: *Lantana camara* L.
Varietal Denomination: LANZ0001

(75) Inventor: Shifeng Pan, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,062

(22) Filed: Oct. 7, 2011

(51) Int. Cl.
*A01H 5/00* (2006.01)

(52) U.S. Cl. ..... Plt./227

(58) Field of Classification Search ..... Plt./227
See application file for complete search history.

*Primary Examiner* — Annette Para
(74) *Attorney, Agent, or Firm* — Joshua L. Price

(57) ABSTRACT

A new *Lantana* plant named 'LANZ0001' particularly distinguished by the large sized, bold yellow flowers that turn orange to red, with excellent floriferousness, a result of limited seed set, and a relatively compact and mounding habit that is well branched with dark green foliage.

1 Drawing Sheet

Latin name of the genus and species of the plant claimed: *Lantana camara* L.

Varietal denomination: 'LANZ0001'.

BACKGROUND OF THE NEW PLANT

The present invention comprises a new *Lantana*, botanically known as *Lantana camara* L., and hereinafter referred to by the variety name 'LANZ0001'.

'LANZ0001' is a product of a planned breeding program. The new cultivar has large sized, bold yellow flowers that turn orange to red, with excellent floriferousness, a result of limited seed set, and a relatively compact and mounding habit that is well branched with dark green foliage.

'LANZ0001' originates from a hybridization in a controlled breeding program in July 2007 in Gilroy, Calif. USA. The female parent was an unpatented, proprietary plant identified as 'G297-2' with lighter rose color, fewer inflorecences, and a smaller plant habit.

The male parent of 'LANZ0001' was identified as 'G314-1', an unpatented, proprietary plant with lighter rose color, smaller inflorescences and smaller foliage. The resultant seed was sown in December 2007.

'LANZ0001' was selected as one flowering plant within the progeny of the stated cross in April 2008 in a controlled environment in Gilroy, Calif.

The first act of asexual reproduction of 'LANZ0001' was accomplished when vegetative cuttings were propagated from the initial selection in the April 2008 in a controlled environment in Gilroy, Calif.

BRIEF SUMMARY OF INVENTION

Horticultural examination of plants grown from cuttings of the plant initiated in Gilroy, Calif., and continuing thereafter, has demonstrated that the combination of characteristics as herein disclosed for 'LANZ0001' are firmly fixed and are retained through successive generations of asexual reproduction.

'LANZ0001' has not been observed under all possible environmental conditions. The phenotype may vary significantly with variations in environment such as temperature, light intensity and day length.

A Plant Breeder's Right for this cultivar was applied for in Canada on Dec. 24, 2010, #10-7127. 'LANZ0001' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

Figure 1:
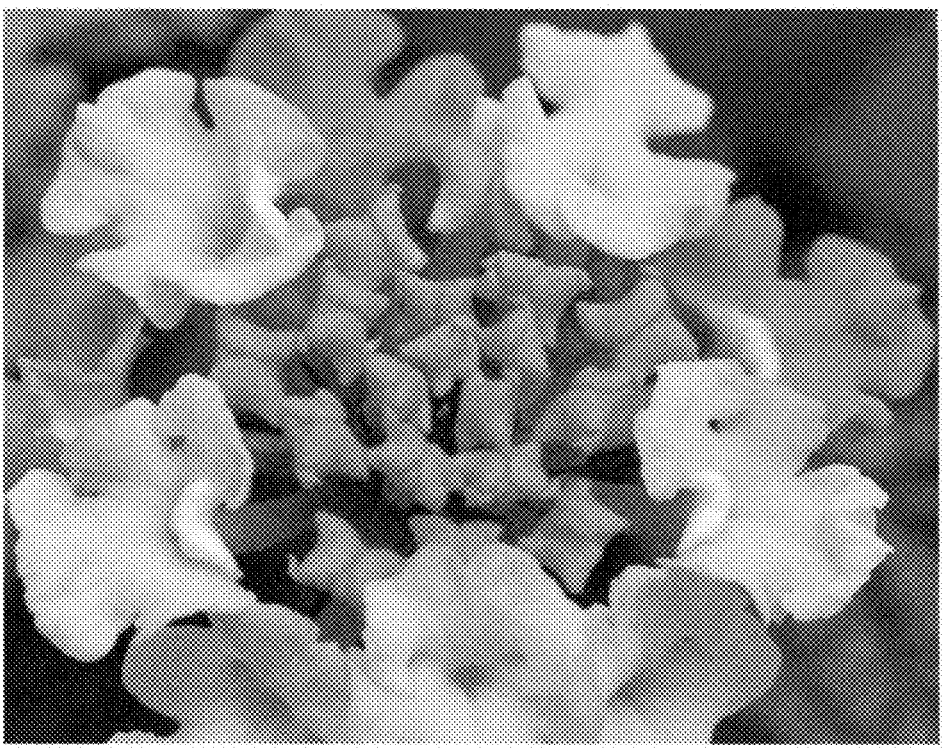
Figure 2:
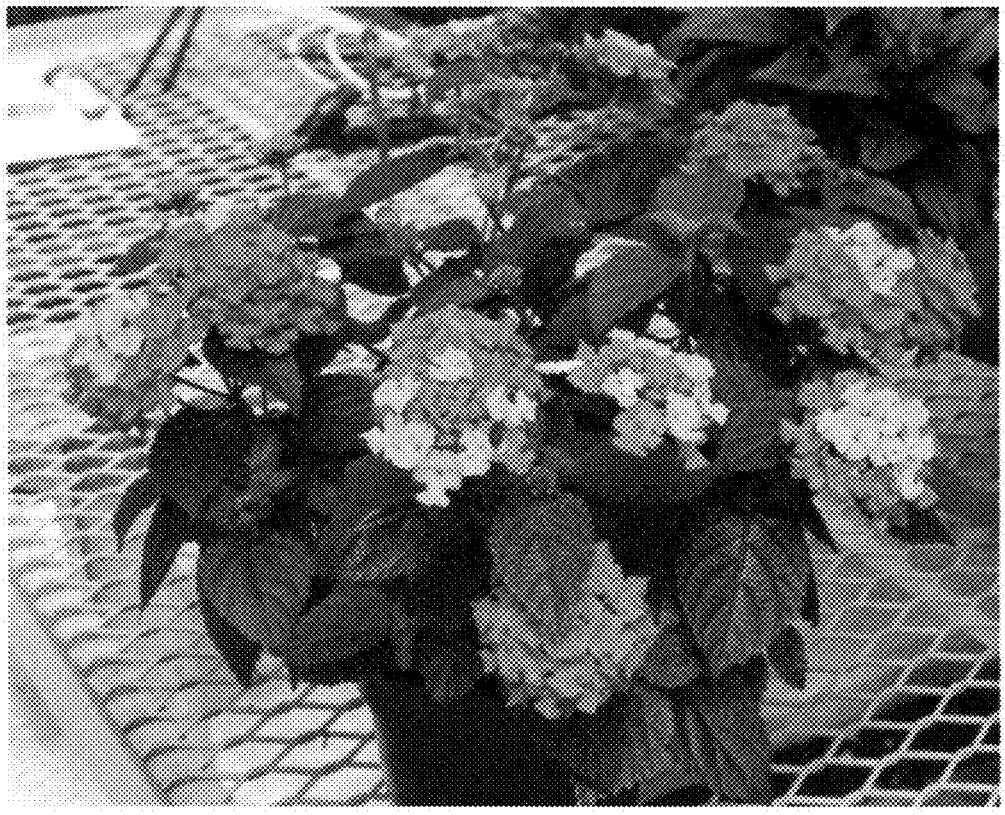

The accompanying photographic drawing shows typical flower and foliage characteristics of 'LANZ0001' with colors being as true as possible with an illustration of this type. The photographic drawing shows in FIG. 1 a close-up of an inflorescence and in FIG. 2, a flowering plant of the new variety.

DETAILED BOTANICAL DESCRIPTION

The plant descriptions, measurements and aforementioned photographs were taken in Gilroy, Calif. in April, 2011 in a greenhouse. These plants were growing in 4.5 inch pots in a trial setting. The plants were about 12 weeks of age and were grown with several early sprays of Paclobutrazol, a plant growth regular.

Color Chart used: Royal Horticultural Society Colour Chart (R.H.S.) 2001

TABLE 1

DIFFERENCES BETWEEN THE NEW VARIETY 'LANZ0001' AND A SIMILAR VARIETY

| | 'LANZ0001' | 'Bante Rossa' (U.S. Plant Pat. No. 18,148) |
|---|---|---|
| Flower timing: | 5-7 days earlier | 5-7 days later |
| Foliage size: | Slightly smaller | Slightly larger |
| Flower color: | Deeper rose | Somewhat lighter rose |

Plant:

*Form, growth and habit.*—Relatively compact and mounding habit, well branched apical pinching enhances the number of branches and results in a tighter plant habit.

*Plant height.*—About 20.0 cm.

*Plant height (inflorescence included).*—20.0-25.0 cm.

*Plant width.*—34.0-45.0 cm.

Foliage:

*Type.*—Opposite.

*Immature, leaf color, upper surface.*—Closest to RHS 137A. Lower surface: Closest to RHS 138A.

*Mature, leaf color, upper surface.*—Closest to RHS 139A but a deeper green. Lower surface: RHS N138B.

*Length.*—5.6-6.0 cm.

*Width.*—4.0-4.3 cm.

*Shape.*—Ovate.

*Base shape.*—Attenuate.

*Apex shape.*—Acute.

*Margin.*—Serrulate.

*Texture.*—Hirsute; glandular hairs on both sides.

*Color of veins, upper surface.*—RHS 144B.

*Color of veins, lower surface.*—RHS 144B.

*Petioles color.*—RHS 144B.

*Petioles length.*—1.5 cm.

*Diameter of petiole.*—0.25 cm.

*Texture.*—Hirsute, pilose, glandular hairs.

Stem:

*Quantity of main stems.*—5-6.

*Color of stem.*—RHS 144B.

*Length of stem.*—16.0-20.0 cm.

*Diameter.*—0.2 cm.

*Length of internodes.*—1.7-3.0 cm.

*Texture.*—Hirsute, pilose, glandular hairs.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 27.

*Quantity of inflorescences per plant.*—At least 25 in various maturity stages.

*Lastingness of individual blooms on the plant.*—About 4 weeks (depending on temperatures).

*Fragrance.*—Slightly spicy.

*Umbel horizontal diameter.*—4.0-4.4 cm.

*Umbel depth.*—2.4 cm.

*Peduncle color.*—RHS 144A.

*Length of peduncle.*—4.0-5.0 cm.

*Peduncle diameter.*—0.15 cm.

*Texture.*—Pilose, hirsute, glandular hairs.

Corolla:

*Floret form.*—Salver-shaped to shallow cup-shaped and zygomorphic, with a relatively long tube at the base.

*Floret horizontal diameter.*—0.8-1.1 cm.

*Floret depth.*—2.0 cm.

*Immature, color of petals, upper surface.*—RHS 6B with tinge of RHS 35B on margins. Lower surface: RHS 5B with RHS 41B.

*Mature, color of petals, upper surface.*—RHS 3B base overlaid RHS 15C with slight hues of RHS 41B at throat on margins; All maturing to RHS 25D overlaid heavily with RHS 51B to RHS 51C in dusty patterns. Lower surface: RHS 29D with shades of RHS 47D.

*Petal length.*—0.5-0.6 cm.

*Petal diameter.*—0.5-0.7 cm.

*Apex.*—Mucronulate.

*Margin.*—Entire.

*Shape.*—Obovate.

*Degree of lobation.*—Moderate.

*Texture, upper surface.*—Papillose. Lower surface: Papillose.

*Corolla tube, color, outer surface.*—RHS 26D overlaid with hues of RHS N34C that increase with intensity with maturity. Color, inner surface: RHS 39D.

*Corolla tube length.*—1.1 cm.

*Diameter (at opening).*—0.2 cm.

*Corolla tube texture, outer surface.*—Pubesccent. Inner surface: Papillose.

Bud (just before opening):

*Color.*—RHS 34A to RHS 34B.

*Length.*—1.0-1.1 cm.

*Width.*—0.3 cm at tip.

*Shape.*—Tubular.

Bract:

*Color.*—RHS 137A.

*Length.*—1.0-1.1 cm.

*Diameter.*—0.3 cm.

*Texture, upper surface.*—Hirsute, glandular hairs. Lower surface: Hirsute, glandular hairs, pilose.

Calyx:

*Number of sepals.*—5 fused sepals forming a short tube around the base of each floret.

*Color of sepals.*—RHS 144D.

*Length of sepals.*—0.2-0.3 cm.

*Width of sepals.*—0.1-0.2 cm.

*Apex shape.*—Obtuse.

*Texture, outer surface.*—Pubescent. Inner surface: Glabrous.

Reproductive organs:

*Pistil.*—1.

*Length.*—0.3-0.4 cm.

*Style color.*—RHS 150D.

*Style length.*—0.3 cm.

*Stigma color.*—About RHS 150C.

*Stamens.*—4.

*Color of filaments.*—RHS 1D.

*Length filaments.*—0.2-0.3 cm.

*Anther color.*—RHS 3C.

*Length of anthers.*—0.1 cm.

*Pollen amount.*—None was really observed.

*Color of pollen.*—Not observed.

*Fertility/seed set.*—Has not been observed on this hybrid.

Disease/pest resistance: Disease/pest resistance has not been observed on this hybrid.

What is claimed is:

1. A new and distinct variety of *Lantana* plant named 'LANZ0001' substantially as illustrated and described herein.

* * * * *